United States Patent [19]

Wagner

[11] Patent Number: 6,150,364

[45] Date of Patent: Nov. 21, 2000

[54] PURIFICATION AND CRYSTALLIZATION OF RIBOFLAVIN

[75] Inventor: Gerhard Wagner, Wehr, Germany

[73] Assignee: Roche Vitamins Inc., Nutley, N.J.

[21] Appl. No.: 09/420,824

[22] Filed: Oct. 19, 1999

[30] Foreign Application Priority Data

Oct. 19, 1998 [EP] European Pat. Off. ............. 98119686

[51] Int. Cl.[7] .................... C07D 475/14; A61K 31/525
[52] U.S. Cl. ............................................ 514/251; 544/251
[58] Field of Search .............................. 544/251; 514/251

[56] References Cited

U.S. PATENT DOCUMENTS

| | | | |
|---|---|---|---|
| 2,324,800 | 7/1943 | Pasternack et al. | 260/211 |
| 2,603,633 | 7/1952 | Dale | 260/211.3 |
| 2,797,215 | 6/1957 | Dale et al. | 260/211.3 |
| 4,687,847 | 8/1987 | Grimmer et al. | 544/251 |
| 5,210,023 | 5/1993 | Grimmer et al. | 514/251 |
| 5,300,303 | 4/1994 | Grimmer et al. | 424/489 |

FOREIGN PATENT DOCUMENTS

| | | |
|---|---|---|
| 633 852 | 12/1985 | Canada . |
| 0 164 704 A2 | 12/1985 | European Pat. Off. . |
| 0 464 582 A2 | 1/1992 | European Pat. Off. . |
| 0 307 767 B1 | 7/1993 | European Pat. Off. . |
| 0 730 034 A1 | 9/1996 | European Pat. Off. . |
| 4 014 262 A1 | 11/1991 | Germany . |

OTHER PUBLICATIONS

Chemical Abstracts, vol. 113, No. 2, abstract No. XP002125630 (1990).

Patent Abstracts of Japan, vol. 14, No. 7 of JP 0125422 A (1990).

*Primary Examiner*—Mukund J. Shah
*Assistant Examiner*—Pavanaram K. Sripada
*Attorney, Agent, or Firm*—Mark E. Waddell; Setphen M. Haracz; Bryan Cave LLP

[57] ABSTRACT

Purified and crystallized riboflavin is prepared by a process that includes dissolving needle-shaped riboflavin of the stable modification A form in an aqueous mineral acid solution at a temperature not exceeding about 30° C. with intensive intermixing. Active charcoal is then added to the resulting solution. After adsorption of the dissolved impurities from the solution onto the active charcoal, the solution containing the active charcoal is subjected to counter-current filtration over a ceramic membrane having a pore size of about 20 to about 200 nm. The resulting filtrate is treated with a five- to ten-fold amount of water (vol./vol.) at a temperature not exceeding about 30° C. The resulting precipitated, spherical crystals of riboflavin are then separated by centrifugation or filtration. If desired, the spherical crystals of riboflavin may be washed with water and subsequently dried. The purified and crystallized riboflavin formed by this process is suitable for pharmaceutical and foodstuff applications.

20 Claims, No Drawings

PURIFICATION AND CRYSTALLIZATION OF RIBOFLAVIN

FIELD OF THE INVENTION

The present invention relates to a process for the purification and crystallization of riboflavin. The riboflavin may then be employed in pharmaceutical and foodstuff applications.

BACKGROUND OF THE INVENTION

Riboflavin commercially available today is produced partly synthetically and partly using biotechnology techniques. Recently, biotechnological processes for producing riboflavin have been in ascendance. In riboflavin fermentative production processes, it is extremely difficult to purify and concentrate riboflavin to the extent required for pharmaceutical and foodstuff applications.

For pharmaceutical and foodstuff applications the fermentatively produced riboflavin to be purified is usually first dissolved in an acidic or alkaline solution. Usually, contaminants, such as cell residue, proteins, peptides, and amino acids which may remain in dissolved or undissolved form after the dissolution of the riboflavin can then be separated from the riboflavin only with a relatively large effort by the combination of several different specific operations.

In conventional processes, dissolved riboflavin is usually crystallized out of solution as needle-shaped crystals that normally correspond to its stable modification A form using a variety of procedures, usually at temperatures above 30° C. (see, for example, U.S. Pat. Nos. 2,324,800, 2,797,215 and 4,687,847).

Furthermore, riboflavin has hitherto been produced and marketed exclusively in the stable crystal modification A form. Riboflavin in this form is soluble in water only to a very limited extent. Thus, the solubility behavior of this form of riboflavin is relatively poor for pharmaceutical and foodstuff applications. Accordingly, for a long time, there has existed the need to improve the solubility behavior and the bioavailability of riboflavin.

Various reports in the literature disclose different stable crystal modifications of riboflavin, which are formed by precipitation from an alkaline solution. From such reports, however, no practical operating process has been developed, presumably due to the chemical degradation of riboflavin in alkaline solutions (see, for example, U.S. Pat. No. 2,603,633).

The riboflavin marketed today is partly in the form of very fine powder and partly in the form of long yellow needles. The fine powder form of riboflavin has a considerable dustiness, an extremely low bulk density, and a poor flow behavior. This form of riboflavin also becomes charged very readily. Consequently, pressing the fine powder form of riboflavin into tablets is hindered, and additives are required to improve its flow and compacting behavior.

Likewise, the riboflavin needles exhibit a strong dust generation when processed and are problematic during further processing, such as, for example, in the vitaminization of flour. Also, various agglomeration procedures carried out during the crystallization process have hitherto not been used for the large-scale production of riboflavin (see, for example, Canadian Patent 633,852 and European Patent 307,767). Additional agglomeration procedures are carried out during the drying step using needle-shaped crystals of modification A (German Offenlegungsschrift 4,014,262).

Accordingly, a need continues to exist for a process that produces a form of riboflavin which possesses substantially better physical properties, such as better flow and dissolution properties and abrasive resistance compared to riboflavin produced by conventional processes, and which has a purity (riboflavin content) of above 98%.

SUMMARY OF THE INVENTION

Accordingly, the present invention provides a process for making a purer riboflavin starting from needle-shaped riboflavin corresponding to the stable modification A form. The riboflavin used as the starting material in this process may itself be produced synthetically or with biotechnology techniques. The process provided by the present invention produces a riboflavin having a riboflavin content above 98% and better flow and dissolution properties compared to conventionally prepared riboflavin material that is currently available. The riboflavin produced according to the present process has an improved bioavailability and improved physical properties, e.g. in tabletting.

One embodiment of the invention is a process for the purification and crystallization of riboflavin that includes the steps of (a) dissolving needle-shaped riboflavin of a stable modification A form in an aqueous mineral acid solution at a temperature not exceeding about 30° C. with intermixing; (b) adding active charcoal to the solution to adsorb dissolved impurities from the solution onto the active charcoal; (c) filtering the solution containing the active charcoal by counter-current filtration over a ceramic membrane having a pore size of about 20 to about 200 nm to form a filtrate; (d) combining a five- to ten-fold amount of water (vol./vol.) at a temperature not exceeding about 30° C. with the filtrate in a crystallizer to form precipitated spherical crystals of riboflavin; and (e) separating the precipitated spherical crystals of riboflavin by centrifugation or filtration.

Another embodiment of the invention is a pharmaceutical composition that includes riboflavin made by the process set forth above.

A further embodiment of the invention is a foodstuff that includes riboflavin made by the process set forth above.

Yet a further embodiment is a process for supplementing a pharmaceutical or foodstuff with riboflavin that includes (a) obtaining purified riboflavin made by the following steps: (i) dissolving needle-shaped riboflavin of a stable modification A form in an aqueous mineral acid solution at a temperature not exceeding about 30° C. with intermixing; (ii) adding active charcoal to the solution to adsorb dissolved impurities from the solution onto the active charcoal; (iii) filtering the solution containing the active charcoal by counter-current filtration over a ceramic membrane having a pore size of about 20 to about 200 nm to form a filtrate; (iv) combining a five- to ten-fold amount of water (vol./vol.) at a temperature not exceeding about 30° C. with the filtrate in a crystallizer to form precipitated spherical crystals of riboflavin; and (v) separating the precipitated spherical crystals of riboflavin by centrifugation or filtration. The riboflavin from step (v) is then combined with a pharmaceutical composition or with a foodstuff.

DETAILED DESCRIPTION OF THE INVENTION

The present invention permits production of riboflavin with improved properties as described above. This process includes a pre-purification step and a crystallization step. The crystallization step is then followed by a drying step.

This process includes dissolving needle-shaped riboflavin of the stable modification A form in an aqueous mineral acid solution at a temperature not exceeding about 30° C. with intensive intermixing. Active charcoal is then added to the resulting solution. After adsorption of the dissolved impurities in the solution onto the active charcoal, the solution is subjected to counter-current filtration over a ceramic membrane having a pore size of about 20 to about 200 nm to separate the charcoal from the solution. The resulting filtrate is treated with a five- to ten-fold amount (vol./vol.) of water (relative to the volume of the solution) at a temperature not exceeding about 30° C. which forms a precipitate of spherical riboflavin crystals. The precipitated, spherical crystals of riboflavin are then separated by centrifugation or filtration.

After the riboflavin crystals have been obtained in this manner, the crystals may, if desired, be washed with water, and subsequently dried according to methods known in the art.

The starting material used in the present process is a needle-shaped riboflavin of modification A, as is obtained, for example, in the production for foodstuffs. For purposes of the present invention, the phrase "needle-shaped riboflavin of modification A" means a composition generally having a riboflavin content of about 85 to about 98%. Depending on its method of manufacture, the total amount of chemical byproducts and/or fermentation residues, as well as water, in the riboflavin starting material are accordingly 2% (wt.) or more.

In the first stage of the process of the present invention, the riboflavin starting material, in dry or filter-moist form, is dissolved in an aqueous mineral acid solution. The dissolution of the starting material takes place by a protonation reaction. In the dissolution procedure, fermentation residues, such as proteins, peptides, and amino acids, and/or chemical byproducts, become liberated and are present in the solution partly dissolved and partly in solid form.

The mineral acid used in the present process may be, for example, hydrochloric acid or nitric acid. Hydrochloric acid is preferred. The concentration of the mineral acid is about 10% to about 65% (wt.).

When an aqueous hydrochloric acid solution is used in the present process, its concentration is in the range of about 18 to about 24% (wt.). Up to about 19% dry riboflavin may be dissolved in such an aqueous hydrochloric acid solution. Such a solution is almost saturated.

Generally, in the dissolution step, the amount of riboflavin relative to the amount of aqueous mineral acid depends on the nature of the mineral acid, the concentration of the solution, and the dissolution temperature.

The dissolution of the needle-shaped riboflavin in the aqueous mineral acid solution is carried out at temperatures up to a maximum of 30° C., preferably at about 5 to about 25° C., such as for example, at about 10 to about 20° C. The solution is preferably subjected to intensive intermixing, for example by intensive stirring. The intensity of such "intensive intermixing" or stirring may be expressed in terms of the energy input/volume. In the present case said energy input/volume of the intensive intermixing is suitably in the range from about 1 to about 3 kW/m², preferably about 2.3 to about 2.5 kW/m².

Increasing the temperature and/or the intensity of the intermixing may reduce the dissolution time of the riboflavin. The overall riboflavin dissolution procedure generally takes up to about 30 minutes, depending on the temperature and intensity of intermixing.

In the next stage of the process, active charcoal is added to the riboflavin/aqueous mineral acid solution. The impurities present in dissolved form are then adsorbed onto the active charcoal.

The active charcoal may be powdered or granulated. In the present process, about 0.5 to about 9% (wt.), preferably about 3% (wt.) (based on the riboflavin content) of the active charcoal is added to the riboflavin/mineral acid solution for the adsorptive removal of the dissolved impurities. Depending on the impurities, the active charcoal may be left in the solution for up to about 12 hours, preferably from about 0.5 to about 3 hours.

In the present process, the active charcoal may be acid-washed active charcoal with a bulk density of about 250 to about 400 kg/m³, preferably about 300 kg/M³, with a specific surface area of about 1200 to about 1600 m²/g, preferably about 1400 m²/g. Preferably, the active charcoal has an average particle size of about 20 to about 70 pm. In the present invention, examples of active charcoals include NORIT® CA1 and BENTONORIT® CA1, which are especially suitable for the adsorption of dissolved biological impurities, as well as NORIT® SX2, which is especially suitable for the separation of chemical impurities.

If desired, in addition to active charcoal, a filter aid may be added to the riboflavin/mineral acid solution. For example, about 2 to about 9% (wt.) (based on the riboflavin content) of a filter aid may be used. Under the term "filter aid" there is generally understood an agent, which, in the case of a suspension with relatively little solid component, enables a filter cake to form which is more easily separated from the surface of the filter upon which it has formed, or, in the case of a filtered medium containing a dense, solid component of a slimy nature, renders the collected filter cake looser in consistency and thus more easily separable than otherwise. The filter aid is, as already mentioned, either added to the riboflavin/mineral acid solution with active charcoal for filtration, or, alternatively, coated onto the filter prior to its use in the filtration. Commonly employed filter aids include cellulose, silica gel, kieselguhr, perlite and sawdust, and function in a physical/mechanical way, i.e. do not exert any chemical effect on the medium being filtered; they are essentially insoluble in said medium. For the purposes of the present process the bulk density of the filter aid is suitably in the range from about 110 to about 300 g/l, and its mean particle size is suitably in the range from about 5 to about 160 microns. Suitable filter aids in the present case include, for example, ARBOCEL® BWW 40 and B 800 from Rettenmaier & Söhne GmbH +Co.

The separation of the active charcoal, the optional filter aid, and any undissolved fermentation residue from the riboflavin/mineral acid solution is carried out by subsequent counter-current filtration. Counter-current filtration is carried out over a ceramic membrane that has a pore size of about 20 to about 200 nm, preferably about 50 nm.

In this process, it has surprisingly been found that, in addition to adsorption, the active charcoal also acts as an abrasive on the covering layer that forms on the ceramic membrane of the counter-current filtration unit. The active charcoal pumped around in the circuit abrasively cleans the covering layer of carbon and fermentation residues formed on the membrane. By this action, it is now possible to operate the membrane in a stable manner over a longer period of time with almost double the throughput than without active charcoal.

As a rule, the counter-current velocity over the membrane is relatively high, for example, about 5 to about 6 m/s. In order not to compress the covering layer excessively, the trans-membrane pressure is maintained at about 1 to 2 bar (0.1 to 0.2 MPa).

After counter-current filtration, the riboflavin/mineral acid solution is caused to precipitate (i.e., crystallize), which is effected by the addition of a five- to ten-fold amount of water (relative to the volume of the riboflavin/mineral acid solution). The resulting deprotonization of the riboflavin present in the aqueous solution leads to its precipitation.

The temperature of the solution in which the crystallization takes place may be varied from about 0 to 30° C., depending on the production method and the degree of impurity of the riboflavin. Especially in the case of synthetically produced riboflavin, the temperature may be increased to 30° C. In the case of fermentative or relatively clean riboflavin, temperatures below 10° C. are generally sufficient to cause precipitation. Preferably, however, a precipitation temperature of about 4 to 10° C. is selected.

The crystallization of riboflavin may be carried out batchwise or continuously, preferably continuously. Cascades or individual vessels may be used as the crystallizer apparatus. Especially in the case of individual vessels, it is preferable to introduce the riboflavin solution at different positions in the vessel. Within the crystallizer, a very good macroscopic intermixing must be set up in every case. This may be accomplished, for example, using a two-stage stirring device, with the feed solutions displaced by 180° that are fed on to upper and lower stirrer levels. To accomplish the crystallization, water is preferably introduced at the upper level and the riboflavin/mineral acid solution is introduced at the lower level.

Stirring should be carried out very carefully to prevent damage to the crystals. Residence time of the solution in the crystallizer may be between about 5 and about 20 minutes, preferably about 10 to 13 minutes. Subsequent filtration is accomplished using a filter or a centrifuge. Preferably, a band filter is used during the filtration. The band filter may be used in the washing step as well. The crystallized riboflavin is then dried using methods known in the art.

Recycling the mother liquor from the washing fluid with the water flowing into the crystallizer may regulate the initial relative supersaturation in the crystallizer (prior to the addition of water). The ratio of mother liquor to water in the crystallizer is preferably about 1:1 to about 1:8. The relative supersaturation may be estimated via the conductivity of the solution present in the crystallizer. Ideally, the conductivity of the solution is maintained at about 170 to about 222 mS/cm. Depending on the conductivity of the solution in the crystallizer, the recycling of the mother liquor may be dispensed with. When the mother liquor is recycled, it is preferably regulated through the conductivity existing in the crystallizer.

Unexpectedly, it has been found that by appropriate selection of mother liquor-to-water mixing ratios, temperatures, intermixing intensity and times, and residence time of the solution in the crystallizer, it is possible in the crystallization stage of the present process to crystallize a more unstable modification form of riboflavin, which is spherical with a spiky surface. This form of riboflavin has a substantially larger surface area than the known needle-shaped crystals of the modification A form. Surprisingly, this spherical crystal product is not the result of an agglomeration procedure as has hitherto been generally described in the literature for spherical crystals (see, for example, European Patent 307,767 and Can. J. Chem. Eng. 47, 166–170 (1969)).

Rather, growth of needle-shaped crystals in the present process is from an initially crystallized-out, small, probably amorphous, crystal seed. The dendritic crystals obtained in this process correspond to the more soluble modification B or C forms of riboflavin, and have adequate storage stability.

Furthermore, because of the more unstable modification and larger surface area of these crystals, they have superior dissolution properties and, by virtue of their spherical shape, outstanding flow properties. Moreover, the process in accordance with the invention affords riboflavin crystals with a higher abrasion resistance than in the case of agglomerates.

As set forth above, the crystallizate is separated by filtration or centrifugation. The filter cake is then preferably washed with water and then dried.

The purified and crystallized riboflavin produced by the process of the present invention is usefully comprised in a foodstuff or a pharmaceutical, especially for the purposes of vitaminization and/or coloration Examples of foodstuffs and pharmaceutical products which may be supplemented with such purified and crystallized riboflavin include flour, cereal products such as cornflakes and muesli, milk and milk products such as milk drinks, ice cream, yoghurt and blancmange-type puddings, mayonnaise, salad dressings, "instant" fruit drinks, sweetening and baking products, multivitamin tablets, pharmaceutical tablets and infusion solutions.

The following examples are provided to further illustrate the present process of purifying and crystallizing riboflavin, as well as certain physical properties of the purified crystallized riboflavin. These examples are illustrative only and are not intended to limit the scope of the invention in any way.

EXAMPLES

Example 1

Purification and Crystallization of Riboflavin

The starting material used for the process described hereinafter was fermentatively produced riboflavin. This starting material had a riboflavin content of 97.02% (according to HPLC), a residual moisture content ($H_2O$) of 0.80%, as well as an amino acid content of 1.11%. The starting riboflavin was present as needle-shaped crystals of the stable modification A form.

350.0 g of this starting riboflavin material was dissolved in 1708.6 g of 24% hydrochloric acid at 22° C. while stirring. After a dissolution period of about 15–20 minutes, a brown-black solution containing about 17% riboflavin was present.

16 g (about 3% of the amount of riboflavin) of active charcoal (NORIT® CA1) was subsequently added to the solution, and the mixture was stirred for an additional 4 hours. The mixture was placed into a double-jacketed feed tank of a laboratory membrane apparatus. The tank was cooled and maintained at a maximum temperature of 35° C. Using a centrifugal pump, the solution was pumped over a ceramic membrane with an effective surface area of 0.0055 $m^2$. The trans-membrane pressure was adjusted to 1.5 bar (0.15 MPa); the counter-current velocity over the membrane was adjusted to 6 m/s. This gave a permeate throughput of about 100 $l/m^2/h$, which was maintained almost to the end of the filtration.

The solution of riboflavin in hydrochloric acid was then crystallized in a continuously operating precipitation crystallizer. The 3 l precipitation crystallizer was first filled with about 2 l of water and the liquid was stirred at 100 rpm with a two-stage inclined flat blade paddle stirrer, and subsequently cooled to 10° C. Thereafter, at about 10° C. 1590 g/h of the solution of riboflavin in hydrochloric acid was continuously added to the crystallizer at the upper stirrer position. Simultaneously and continuously about 9000 g/h of water was added to the crystallizer at the lower stirrer position.

About 2–4 minutes after the riboflavin/hydrochloric acid solution had been added to the precipitation crystallizer, the riboflavin began to crystallize out of solution as orange-yellow crystals. Initially, the separated crystals appeared to be flocculent. After 20–30 minutes, the crystals changed into granular particles. The crystal suspension was then drained off continuously until the 3 l mark (double jacket end) had been reached in the crystallizer (i.e., after about 7 minutes). The valve was then adjusted so that the level remained approximately at the 3 l mark. The discharged suspension was added directly to a P3 suction filter where the solid was separated from the solution.

About 2500 ml of suspension was collected every 15 minutes and a filter cake of about 1 cm thickness was obtained. This was then washed in portions with 1300 ml of water until a pH of about 5 had been reached.

The moist, yellow crystallizate (65–75% residual moisture) was subsequently dried.

Example 2

Purification and Crystallization of Riboflavin Using a Counter-Current Membrane Pore Size of 50 nm A riboflavin solution was produced and treated with active charcoal as described in Example 1. In contrast to Example 1, the solution was purified over a membrane having a pore size of about 50 nm. The trans-membrane pressure was 1.5 to 1.7 bar (0.15 to 0.17 MPa) and the counter-current velocity was 5 to 6 m/s. This gave a permeate throughput of about 70 l/m$^2$/h. The crystallization, filtration, and washing were carried out as described in Example 1. The crystallization temperature was maintained between 9 and 10° C. The crystallizate was dried in a laboratory drying oven at 100° C.

Example 3

Purification and Crystallization of Riboflavin from a Synthetically Derived Source In this example, the starting material was chemically produced and had a riboflavin content of 98%. The starting material was dissolved as described in Example 1. The counter-current filtration was carried out as described in Example 2. The crystallization was carried out at 20° C. by adding 1030 g/h of a riboflavin/hydrochloric acid solution and 15060 g/h of water to a precipitation crystallizer. Filtration and washing were carried out as described in Example 1. The crystallizate was dried as described in Example 2.

The results of Examples 1–3 are compiled in Table 1 below:

TABLE 1

Purities and Properties of the Respective Dried Final Product

| Example | Modification (according to X-ray structural analysis) | Riboflavin content (according to HPLC) | Lumichrome content (according to HPLC) | Lumiflavin content (according to HPLC) | Amino acid Content |
|---|---|---|---|---|---|
| 1 | B | 98% | 0.08% | — | 0.1% |
| 2 | B | 98.9% | 0.15% | — | 0.06% |
| 3 | B | 99% | 0.15% | 0.25% | — |

The respective missing percentages include the water content and further slight impurities present.

The invention being thus described, it will be obvious that the same may be varied in many ways. Such variations are not to be regarded as a departure from the spirit and scope of the invention, and all such modifications are intended to be included within the scope of the following claims.

We claim:
1. A process for the purification and crystallization of riboflavin comprising the steps of:
  (a) dissolving needle-shaped riboflavin of a stable modification A form in an aqueous mineral acid solution at a temperature not exceeding about 30° C. with intermixing;
  (b) adding active charcoal to the solution to adsorb dissolved impurities from the solution onto the active charcoal;
  (c) filtering the solution containing the active charcoal by counter-current filtration over a ceramic membrane having a pore size of about 20 to about 200 nm to form a filtrate;
  (d) combining a five- to ten-fold amount of water (vol./vol.) at a temperature not exceeding about 30° C. with the filtrate in a crystallizer to form precipitated spherical crystals of riboflavin; and
  (e) separating the precipitated spherical crystals of riboflavin by centrifugation or filtration.

2. A process according to claim 1 wherein the mineral acid is hydrochloric acid or nitric acid.

3. A process according to claim 2 wherein the mineral acid is hydrochloric acid.

4. A process according to claim 1 wherein step (a) is carried out at about 5 to about 25° C.

5. A process according to claim 4 wherein step (a) is carried out at about 10 to about 20° C.

6. A process according to claim 1 wherein about 0.5 to about 9% (weight percent relative to the riboflavin content) of the active carbon is added in step (b).

7. A process according to claim 6 wherein about 3% (weight percent relative to the riboflavin content) of the active carbon is added in step (b).

8. A process according to claim 1 wherein the active charcoal in step (b) is an acid-washed active charcoal having a bulk density of about 250 to about 400 kg/m$^3$, a specific surface area of about 1200 to about 1600 m$^2$/g, and an average particle size of about 20 to about 70 μm.

9. A process according to claim 8 wherein the active charcoal in step (b) is an acid-washed active charcoal having a bulk density of about 300 kg/m$^3$, a specific surface area of about 1400 m$^2$/g, and an average particle size of about 20 to about 70 μm.

10. A process according to claim 1 further comprising adding a filter aid in step (b).

11. A process according to claim 1 wherein the ceramic membrane has a pore size of about 50 nm.

12. A process according to claim 1 wherein the temperature of the solution in step (d) is about 4 to about 10° C.

13. A process according to claim 1 wherein step (d) is carried out continuously and wherein residence time of the solution in the crystallizer during step (d) is about 5 to about 25 minutes.

14. A process according to claim 13 wherein residence time of the solution in the crystallizer during step (d) is about 10 to 13 minutes.

15. A process according to claim 1 further comprising the steps of collecting, separating, and drying the precipitated, spherical crystals of riboflavin on a band filter.

16. A process according to claim 1 further comprising intensively intermixing the riboflavin and mineral acid solution in step (a).

17. A process according to claim 1 further comprising washing the spherical crystals of riboflavin with water and subsequently drying the riboflavin.

18. A pharmaceutical composition comprising riboflavin prepared by the process of claim 1.

19. A foodstuff comprising riboflavin prepared by the process of claim 1.

20. A process for supplementing a pharmaceutical or foodstuff with riboflavin comprising:

(a) obtaining purified riboflavin made by the following steps:
  (i) dissolving needle-shaped riboflavin of a stable modification A form in an aqueous mineral acid solution at a temperature not exceeding about 30° C. with intermixing;
  (ii) adding active charcoal to the solution to adsorb dissolved impurities from the solution onto the active charcoal;
  (iii) filtering the solution containing the active charcoal by counter-current filtration over a ceramic membrane having a pore size of about 20 to about 200 nm to form a filtrate;
  (iv) combining a five- to ten-fold amount of water (vol./vol.) at a temperature not exceeding about 30° C. with the filtrate in a crystallizer to form precipitated spherical crystals of riboflavin; and
  (v) separating the precipitated spherical crystals of riboflavin by centrifugation or filtration; and (b) combining the riboflavin from step (v) with a pharmaceutical composition or foodstuff.

* * * * *

UNITED STATES PATENT AND TRADEMARK OFFICE
CERTIFICATE OF CORRECTION

PATENT NO. : 6,150,364
DATED : November 21, 2000
INVENTOR(S) : Gerhard Wagner

It is certified that error appears in the above-identified patent and that said Letters Patent is hereby corrected as shown below:

Title page,
Item [73], Assignee, the address is incorrect. Please delete "Nutley" and insert -- Parsippany --.

Signed and Sealed this

Eleventh Day of December, 2001

*Attest:*

NICHOLAS P. GODICI
*Attesting Officer* *Acting Director of the United States Patent and Trademark Office*